United States Patent [19]
Mikos et al.

[11] Patent Number: 5,512,600
[45] Date of Patent: Apr. 30, 1996

[54] PREPARATION OF BONDED FIBER STRUCTURES FOR CELL IMPLANTATION

[75] Inventors: Antonios G. Mikos, Houston, Tex.; Robert S. Langer, Newton, Mass.

[73] Assignee: Massachusetts Institute of Technology, Cambridge, Mass.

[21] Appl. No.: 5,910

[22] Filed: Jan. 15, 1993

[51] Int. Cl.$^6$ .................................................. C08K 9/00
[52] U.S. Cl. ............................ 521/61; 521/62; 521/68; 521/76; 523/113; 435/240.23; 19/161.1; 424/436; 424/426
[58] Field of Search ................................ 521/61, 62, 68, 521/76; 523/113; 435/240.23; 19/161.1; 424/426, 423

[56] References Cited

U.S. PATENT DOCUMENTS

| | | | |
|---|---|---|---|
| 4,520,821 | 6/1985 | Schmidt et al. | 128/334 R |
| 5,100,783 | 3/1992 | Dean et al. | 435/69.1 |
| 5,185,408 | 2/1993 | Tang | 525/415 |
| 5,290,494 | 3/1994 | Coombes et al. | 264/41 |

OTHER PUBLICATIONS

Cima, L. G., et al., "Tissue Engineering by Cell Transplantation Using Degradable Polymer Substrates," *J. Biomech. Eng.*, 113, 143–151 (1991)/ May.

Jamshidi, K., et al., "Thermal Characterization of Polylactides," *Polymer*, 29. 2229–2234 (1988),. Dec.

Keville, K. M., et al., "Preparation and Characterization of Monodisperse Polymer Microspheroids," *J. Colloid Interface Sci.*, 144, 103–126 (1991)., Jun.

Vacanti, C., "Synthetic Polymers Seeded with Chondrocytes Provide a Template for New Cartilage Formation," *Plast. Reconstr. Surg.*, 88, 753–759 (1991). Oct.

Vacanti, Joseph P., "Beyond Transplantation," *Arch. Surg.*, 123, 545–549 (1988)., May.

Vacanti, Joseph P., et al., "Selective Cell Transplantation Using Bioabsorbable Artificial Polymers as Matrices," *J. Pediatr. Surg.*, 23, 3–9 (1988)., Jan.

*Primary Examiner*—James J. Seidleck
*Assistant Examiner*—R. F. Johnson
*Attorney, Agent, or Firm*—Arnall Golden & Gregory

[57] ABSTRACT

A novel processing technique is reported to bond non-woven fibers and, thus, prepare structural interconnecting fiber networks with different shapes for organ implants. The fibers are physically joined without any surface or bulk modification and have their initial diameter.

5 Claims, 2 Drawing Sheets

PREPARATION OF BONDED FIBER STRUCTURES FOR CELL IMPLANTATION

BACKGROUND OF THE INVENTION

The present invention is in the general area of polymeric device processing and in particular is a method of making bonded fiber structures of biocompatible polymers for use in cell culture and implantation.

The use of biodegradable polymers to regenerate metabolic organs, such as the liver and pancreas, and repair structural tissues like cartilage and bone by cell transplantation was recently reviewed by Cima, et al., "Hepatocyte Culture on Biodegradable Polymeric Substrates," *Biotechn. Bioeng.*, 38, 145–158 (1991); Langer, et al., "Future Directions in Biomaterials," *Biomaterials*, 11, 738–745 (1990); Vatanti et al., "Selective Cell Transplantation Using Bioabsorbable Artificial Polymers as Matrices," *J. Pediatr. Surg.*, 23, 3–9 (1988); and Vacanti, "Beyond Transplantation," *Arch. Surg.*, 123, 545–549 (1988). To create organ function, donor material is obtained, the tissue is dissociated into individual cells, the cells are attached to a proper device, and the device is implanted to a place where the immobilized cells grow and function.

In addition to being adhesive substrates for cells, promoting cell growth, and allowing retention of differentiated cell function, materials used as templates for cell transplantation must be biocompatible and biodegradable, processable into desirable shapes, highly porous with large surface/volume ratios, and, finally, mechanically strong.

The polymer provides a sturdy scaffold to the transplanted cells and the means of organization to the ingrowing tissue. High porosity values are required in order to accommodate a large number of cells. As most cells are anchorage-dependent, large values of the total pore area are necessary for high cell growth rates. Also, the pore diameter or the interstitial distance must be much larger than the particular cell diameter and an interconnecting pore network structure is essential for tissue ingrowth, vascularization, and diffusion of nutrients, as reviewed by Vacanti, "Synthetic Polymers Seeded with Chondrocytes Provide a Template for New Cartilage Formation," *Plast. Reconstr. Surg.*, 88, 753–759 (1991).

Poly(lactic-co-glycolic acid) (PLGA) fiber tassels and fiber-based felts fulfill many of the above material requirements and were initially utilized, as reported by Vacanti (1991) and Cima, et al., "Tissue Engineering by Cell Transplantation Using Degradable Polymer Substrates," *J. Biomech. Eng.*, 113, 143–151 (1991), as transplantation devices for hepatocytes and chondrocytes to regenerate liver and cartilage function, respectively. In a recent paper, Freed, et al., "Neocartilage Formation In Vitro and In Vivo Using Cells Cultured on Synthetic Biodegradable Polymers," *J. Biomed. Mater. Res.*, (in press), showed that chondrocytes cultured in vitro on poly(glycolic acid) (PGA) fiber meshes yielded after six weeks a cell density 8.3-fold higher than that at the first day and equaled the cellularity reported for normal bovine articular cartilage. However, although tassels and felts were useful in demonstrating the feasibility of organ regeneration, they sometimes lack the necessary structural stability. In order to be used for cell attachment and transplantation, they must often be configured into shapes similar to those of the repaired tissues, and also provide a firm substrate to the transplanted cells.

There remains a need for an improved method for making polymeric substrates for use in cell culture and implantation, which is efficient, economical and reproducible.

There is a further need for a method which yields polymeric matrices with the appropriate structure and porosity for use in maintaining cell viability and surfaces for attachment following implantation, even when cell masses and internal pressures on the implant increase.

SUMMARY OF THE INVENTION

A method was developed to prepare three-dimensional structures with desired shapes for use as templates for cell transplantation. Both biodegradable and degradable biocompatible synthetic polymers can be used. The resulting materials are highly porous with large surface/volume and provide the necessary space for attachment and proliferation of the transplanted cells. The processing technique calls for the formation of a composite material with non-bonded fibers embedded in a matrix followed by thermal treatment and the selective dissolution of the matrix.

An example of the method uses poly(glycolic acid) (PGA) fiber meshes bonded using poly(L-lactic acid) (PLLA) as a matrix. The bonded structures are highly porous with values of porosity up to 0.81 and area/volume ratios as high as 0.05 $\mu m^{-1}$.

DETAILED DESCRIPTION OF THE INVENTION

The process involves (1) selection of polymers to form fibers and to form a matrix around the polymeric fibers, (2) selection of a solvent or temperatures required to produce a solution of the matrix polymer that does not liquify the fiber polymer, (3) solidification of the matrix polymer around and between the polymeric fibers, (4) heat treatment of the fiber-matrix to immobilize the fibers where they overlap or are crosslinked and (5) removal of the matrix polymer to leave immobilized crosslinked fibers.

SELECTION OF POLYMERS

Synthetic biocompatible polymers may be biodegradable, either by enzymatic action or hydrolysis, or non-biodegradable. Biodegradable polymers are preferred. Such polymers are commercially available or can be synthesized using methods published in the literature and known to those skilled in the art. Examples of biodegradable materials include polymers which degrade by surface erosion or bulk erosion such as poly(lactic acid) (PLLA), poly(glycolic acid) (PGA), poly(lactide-co-glycolide) (PLGA), polyorthoesters, polyanhydrides, polyphosphazines, and blends and copolymers thereof. Examples of non-biodegradable polymers include ethylene vinyl acetate and polymers of acrylic acid and methacrylic acid. Biodegradable materials are preferred for implantation.

Suitable solvent systems and relative melting temperatures are published in standard textbooks and publications. Many of these materials can be formed into fibers by standard processing techniques such as melt extrusion and spin casting, or are commercially available in woven or non-woven form or as sutures.

PROCESSING CONDITIONS

Figure 1:
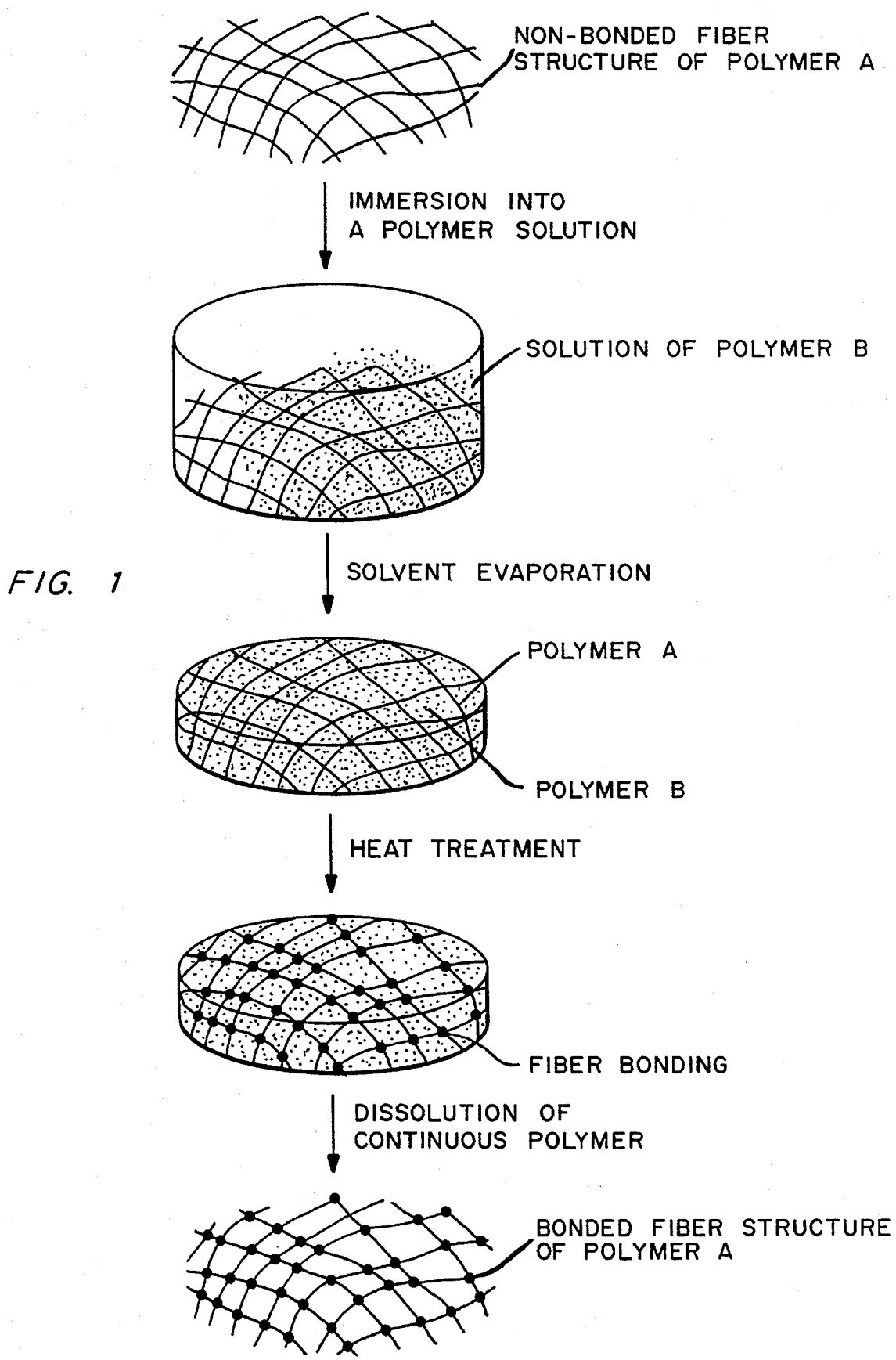
FIG. 1 is a schematic of the steps in the processing technique to bond non-woven polymeric fibers.
Figure 2A:
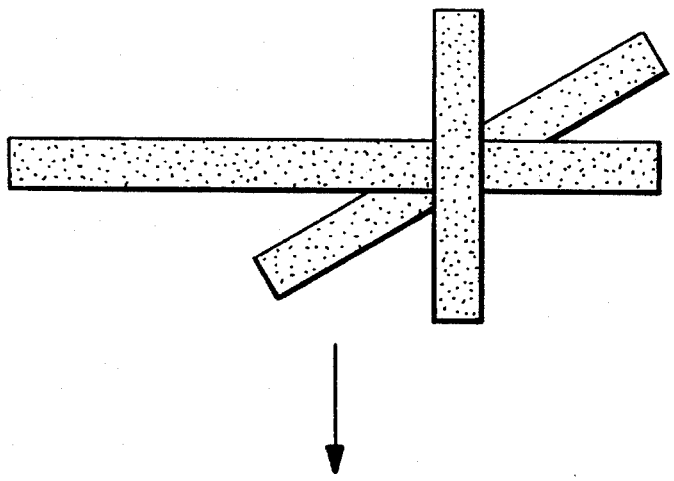
FIG. 2A, 2B, 2C and 2D are schematic presentations of the change of fiber configuration upon heating of a PLLA-PGA composite material at a temperature above the PLLA and PGA melting temperatures.
Figure 2B:
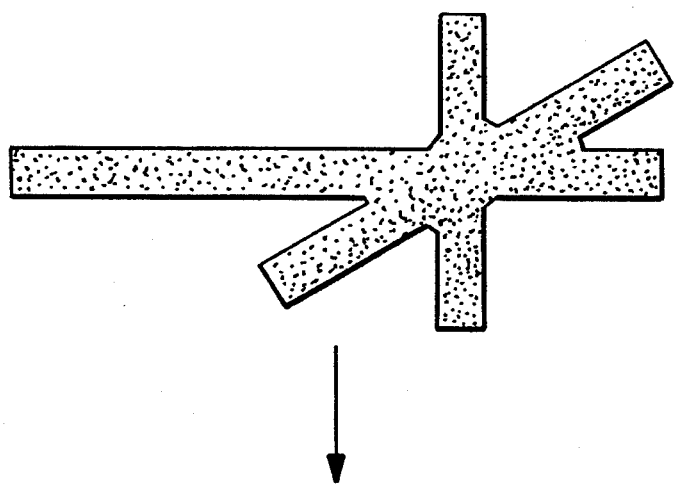
Figure 2C:
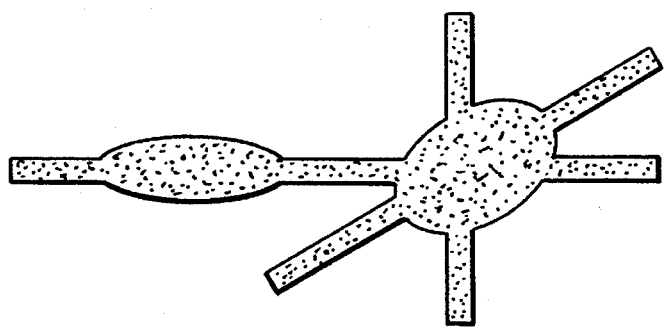
Figure 2D:
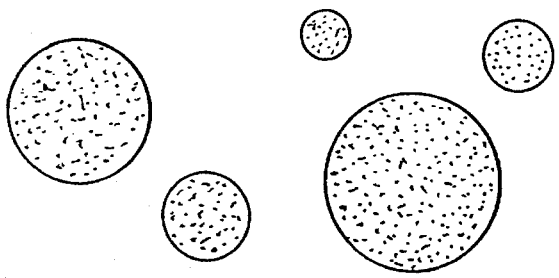

The generalized scheme to bond non-woven fibers involves four steps which are depicted in FIG. 1, once the polymers have been selected.

First, a non-bonded fiber structure of polymer A is immersed in a solution of polymer B or a solution of polymer B is poured into a mold containing a non-bonded fiber structure of polymer A. The solution is formed either by dissolution of polymer B in a solvent which is a non-solvent for polymer A, or by melting polymer B at a temperature less than the melting temperature of polymer A. Polymers A and B must also be incompatible so they are immiscible in their melt state.

Second, the solvent is allowed to evaporate, or the melted polymer allowed to cool, resulting in the formation of a polymer-polymer composite consisting of fibers of polymer A embedded in a matrix of polymer B.

Third, the composite is heated above the melting temperature of polymer A, where the matrix is formed by solvent evaporation, for a short time period to weld the fibers at their cross-points.

Fourth, polymer B is selectively liquified to produce a bonded fiber structure.

In the preferred embodiment, the melting temperature of polymer A is less than the melting temperature of polymer B, the matrix is formed by solvent evaporation of the solution of polymer B around fibers of polymer A, the fibers are welded by heating of the fiber-matrix composite, and the matrix is removed by dissolution in a non-solvent for polymer A.

The resulting polymeric fibrous structure.

The resulting polymeric structure is fibrous, with the crosspoints or fiber interfaces secured by the second polymer blending with the first polymer which forms the fibers as a result of the heat treatment. For use in culturing of mammalian cells, in particular for implantation, the fibrous matrix has a porosity of between approximately 100 and 500 microns, although a range of 50 microns to millimeters can be useful. Fibers need only to be sufficiently large enough in diameter to provide a site of attachment for the cells, generally, in excess of a few microns.

The present invention is further exemplified by the following non-limiting example.

This processing technique was evaluated by binding poly(glycolic acid) (PGA; polymer A) fibers embedded in a poly(L-lactic acid) (PLLA; polymer B) matrix. The PLLA-PGA composite was prepared by casting of a methylene chloride solution of PLLA into a petri-dish containing a PGA non-woven fiber mesh. PLLA, which is incompatible with PGA, was dissolved after heat treatment by methylene chloride to yield a bonded PGA fiber mesh. Methylene chloride, which is a good solvent for PLLA and a non-solvent for PGA, was also selected because of its high volatility (its normal boiling temperature is 39.8° C.).

EXAMPLE 1: PREPARATION OF POLYMERIC COMPOSITE.

Materials

Poly(glycolic acid) (PGA) non-woven fiber meshes were isolated from a multi-laminated fabricate of approximate thickness 0.15 cm and fiber density 8.5 mg/cm² (Acufex Microsurgical, Mansfield, Mass.). The fiber diameter was 14 μm and the PGA viscosity average molecular weight was 60,000. Poly(L-lactic acid) (PLLA) was supplied by Medisorb (Cincinnati, Ohio). The polymer number average molecular weight was determined by gel permeation chromatography (Perkin-Elmer, Series 10, Newton Centre, Mass.) as $M_n=105,000$ ($M_w/M_n=1.13$), where $M_w$ is the weight average molecular weight and $M_n$ is the number average molecular weight. Methylene chloride was furnished by Mallinckrodt (Paris, Ky.).

METHODS

1. Preparation of Composite Membranes

In a typical experiment, 1 g of PLLA was dissolved in 8 ml of methylene chloride. The polymer solution was cast into a petri-dish of 5 cm diameter containing a non-woven mesh of PGA fibers with a weight of approximately 0.02 g. The bottom of the petri-dish was covered with an aluminum backed overlay (Cole-Parmer, Chicago, Ill.) to prevent the adhesion of the produced composite membrane to the glass bottom during the heat treatment step. The covered petri-dish was placed in a fume hood for 24 hours. Residual amounts of methylene chloride were removed by vacuum-drying at 100 μm Hg for 24 hours.

2. Heat Treatment

PLLA-PGA composite membranes placed in covered glass petri-dishes were heated in a convection oven (Model OV-490A-3, Blue M, Blue Island, Ill.) at a temperature $T_1=195°$ C. for $t_1=90$ min and at a higher temperature $T_2$ for $t_2$ min. They were then taken from the oven and were immediately immersed in liquid nitrogen for 15 min. The quenched membranes were air-dried for 15 min before they were vacuum-dried at 100 μm Hg for 24 hours. The drying was essential so as to remove any condensed water vapors. The values of $T_2$, $t_2$, and those of the time, $t_{12}$, required to reach the temperature $T_2$ from that of $T_1$ are presented in Table I. Control samples of PGA non-woven fiber meshes were also heated under the same conditions as the PLLA-PGA composite membranes. The previously mentioned temperatures correspond to the interior of the oven. Because of heat transfer limitations due to the covered glass petri-dish containing the sample, the temperature in the sample is expected to be slightly lower than the oven temperature. The temperature accuracy of the oven was ±1° C.

TABLE I

| | Heat Treatment Conditions of PLLA-PGA Composite Membranes | | | | |
|---|---|---|---|---|---|
| Sample | $T_1$ (°C.) | $t_1$ (min) | $t_{12}$ (min) | $T_2$ (°C.) | $t_2$ (min) |
| 1 | 195 | 90 | 6 | 230 | 5 |
| 2 | 195 | 90 | 7 | 235 | 5 |
| 3 | 195 | 90 | 9 | 240 | 5 |
| 4 | 195 | 90 | 7 | 235 | 7.5 |
| 5 | 195 | 90 | 7 | 235 | 10 |

3. Dissolution of Matrix

After heat treatment, the PLLA matrix of a PLLA-PGA composite membrane was selectively dissolved in 8 ml of methylene chloride for 75 min (the methylene chloride was changed every 15 min). The bonded PGA fibers were vacuum-dried at 100 μm Hg for 24 hours and stored in a desiccator under vacuum until use.

CHARACTERIZATION

1. Light Microscopy

A zoom macroscope (Model M420, Wild Heerbrugg, Heerbrugg, Switzerland) was used to observe the structure of composite membranes before the dissolution of the matrix. The total magnification of the micrographs was 40X.

2. Scanning Electron Microscopy

The samples were coated with gold using a Sputter Coater (Model Desk II, Denton Vacuum, Cherry Hill, N.J.). The gas pressure was set at 50 mTorr and the current was 40 mA for a coating time of 75 s. Cell cultures were first fixed in Karnovsky's fixative at 37° C. for one hour, washed with 0.1M cacodylate buffer (pH 7.4), postfixed for 1 hour in 1% osmium tetroxide, dehydrated in a graded series of ethanol/water solutions, dried in a critical point drier (Ladd Research, Burlington, Vt.) with supercritical $CO_2$, and then were sputter-coated with gold. A Hitachi (Model S-530) Scanning Electron Microscope was used in the studies and was operated at a 15 kV voltage.

3. Mercury Porosimetry

The void volume of PLLA-PGA composite membranes as well as the porosity and the area/volume ratio of bonded PGA fibers were measured by mercury intrusion porosimetry (model Poresizer 9320, Micromeritics, Norcross, Ga.). A solid penetrometer with 5 ml bulb volume (Model 920-61707-00, Micromeritics) was used with samples of approximate weight 0.15 g for composite membranes and 0.005 g for fibers. The filling pressure of the penetrometer was 0.5 psi and the maximum pressure was 30 psi. At the pressure of 30 psi, the total intrusion volume had reached a plateau value. The PGA fiber density used to calculate the porosity from the measured value of the intrusion volume was determined by micropycnometry (model Accupyc 1330, Micromeritics) as 1.68 g/ml.

4. Differential Scanning Calorimetry

A 7 Series Thermal Analysis system of Perkin-Elmer was utilized to measure melting (and crystallization) enthalpy changes of a variety of materials. For composite membranes, approximately 10 mg of sample were tested, and for fibers, 1 mg. A heating rate of 10° C./min was applied in all measurements.

Photomicrographs of PLLA-PGA composite membranes heated at 195° C. for 90 min and three different temperatures of 230° C., 235° C., and 240° C. for 5 min were compared. For the temperature of 230° C., no fiber bonding was observed. Contrary to welding of amorphous polymers at temperatures slightly above the polymer glass transition temperature, bonding of semicrystalline fibers only occurred above the fiber melting temperature. For composites heated at 235° C., patterns of joined fibers were detected, whereas at 240° C. a different morphology of dispersed globules was evident. The cylindrical fiber geometry is not a stable one for melts. A sphere possesses the minimum surface for the same volume and is energetically favored. Thus, the dispersed fibers of a composite material are gradually transformed into spherical domains at temperatures above the highest melting temperature to minimize the total interfacial energy.

The morphology evolution of a melted polymer-polymer fiber composite is illustrated in FIGS. 2A, 2B, 2C, and 2D. At short times, the PGA melting results in joint welding of the fibers at their cross-points and the formation of an interconnecting fiber network structure similar to that of the initially non-bonded fibers. The minimization of the total interfacial energy calls for the growth of the fiber cross-points and the formation of globules along the fiber strands. Consequently, the diameter of the remaining cylindrical fiber strands gets smaller and smaller and eventually the initial fiber composite disappears yielding a new composite consisting of PGA spherical domains embedded in PLLA.

SEM photomicrographs of bonded fiber meshes produced by the dissolution of the PLLA matrix of PLLA-PGA composite membranes heated at 235° C. for 5 min and 7.5 min support the above mechanism of fiber bonding. At 5 min, the fibers were joined at their cross-points without any macroscopic change of the fiber geometry. The porosity of the bonded fiber mesh was measured by mercury porosimetry as 0.81 and its area/volume ratio as 0.05 $\mu m^{-1}$. These values are typical of materials used for cell transplantation. At 7.5 min, globules were developed not only at fiber intersections but also along individual fiber strands. For composites heated at 235° C. for 10 min, only scattered microparticulate and agglomerate structures were recovered after the dissolution of the PLLA matrix.

The importance of the formation of a polymer-polymer composite formed of a fiber mesh embedded in another polymer was evaluated by comparing the morphology of PGA non-woven fiber meshes heated at 195° C. for 90 min and 235° C. for 5 min while embedded in PLLA and surrounded by air. From the SEM photomicrographs of the produced structures, it is deduced that the PLLA matrix prevents the destruction of the fiber configuration observed for the plain PGA fiber mesh and confines the melted PGA in a fiber like shape. Also, PGA fiber meshes without the PLLA matrix heated at temperatures above their melting temperature in air collapsed and did not retain their initial three dimensional shape.

The dynamic behavior of the dispersed phase depended on the rheological properties of both the fiber and the matrix. The terminal relaxation time of entangled polymers in a melt scales to the cube of the chain molecular weight and decreases exponentially with temperature, as described by DeGennes, *Scaling Concepts in Polymer Physics,* Cornell University Press, Ithaca, 1979, and Tirrell, "Polymer Self-Diffusion in Entangled Systems," *Rubber Chem. Technol.,* 57, 523–556 (1984), the teachings of which are incorporated by reference herein. The interfacial tension between polymers does not vary significantly with the molecular weight and the temperature, as reported by Wu, *Polymer Interface and Adhesion,* Marcel Dekker, New York, 1982, and is not expected to affect the fiber transformation. Thus, one infers that the higher the molecular weight of the surrounding matrix, the smaller the fiber distortion under the same processing conditions. The crosslinking of the matrix may also limit the extent of fiber distortion. Keville et al., "Preparation and Characterization of Monodisperse Polymer Microspheroids," *J. Colloid Interface Sci.,* 144, 103–126 (1991), reported a technique to prepare monodisperse polymer microspheroids by uniaxial deformation of a composite material consisting of polymer microparticles embedded in a crosslinked matrix.

In addition to being incompatible with PGA, PLLA was also selected as an embedding medium because it melts at a lower temperature than PGA. From DSC measurements, $T_m=173.7°$ C. for PLLA, and $T_{m1}=217.7°$ C. and $T_{m2}=224.2°$ C. for PGA. The rationale for heating PLLA-PGA membranes at 195° C. (i.e., at a temperature above the melting temperature of PLLA and below that of PGA) for 90 min was to melt the PLLA and fill the pores within the membrane. Composite membranes produced by solvent evaporation are porous and their porosity depends on the size and the relative amount of the dispersed phase. Thus, the melting of the dispersed phase is confined to its volume. The void volume of a PLLA-PGA composite as measured by mercury porosimetry was 0.14 ml/g before and 0.04 ml/g after heating at 195° C. for 90 min.

Provided that the degree of crystallinity of a solvent cast membrane is not affected by the presence of a dispersed phase, from the thermogram of the methylene chloride cast PLLA-PGA membrane, the relative amounts of each polymer can be calculated as:

$$\frac{w_A}{1-w_A} = \frac{\Delta H_{mA}/\Delta H°_{mA}}{\Delta H_{mB}/\Delta H°_{mB}}$$

Here, $w_A$ is the weight fraction of polymer A (PGA), $\Delta H_{mA}$ and $\Delta H_{mB}$ are the measured enthalpies of melting of polymers A and B (PLLA) per gram of composite material. The symbols $\Delta H°_{mA}$ and $\Delta H°_{mB}$ also designate the enthalpies of melting per gram of pure polymer. From the DSC thermograms of PGA fibers and a methylene chloride cast PLLA membrane, the value of $\Delta H°_{mA}$ was measured as 74.1 J/g and that of $\Delta H°_{mB}$ as 49.0 J/g. These values correspond to degrees of crystallinity of 0.39 for PGA and 0.24 for PLLA. (The values of the enthalpies of melting of 100% crystallized polymers used in the calculations were 191.2 J/g for PGA, as reported in Chu and Browning, "The Study of Thermal and Gross Morphologic Properties of Polyglycolic Acid upon Annealing and Degradation Treatments," *J. Biomed. Mater. Res.*, 22, 699–712 (1988), and 203.4 for PLLA, as reported by Jamshidi, et al., "Thermal Characterization of Polylactides," *Polymer*, 29, 2229–2234 (1988). The value of $w_A$ was calculated as 0.03 from the DSC thermogram.

From the measured values of the enthalpies of crystallization and melting for PLLA of a sample heated at 195° C. for 90 min and 235° C. for 5 min and quenched with liquid nitrogen, the PLLA matrix was found to be 100% amorphous. Nevertheless, the crystallinity of the bonded PGA fibers as calculated from the integration of the area under the peaks of $T_{m1}$=221.2° C. and $T_{m2}$=231.5° C. was also 0.39. The PGA fibers, while embedded in PLLA, were annealed for over 90 min, resulting in lamellar thickening of the existing crystallites. This annealing process caused an increase in the melting temperature of PGA by about 5° C. When the fibers were heated to 235° C. for 5 min, part of the crystallites melted. Thus, the sequence of annealing and partial melting explains why the degree of crystallinity of PGA appeared invariant. The absence of any endothermic peaks at 174° C. in the DSC thermogram of the bonded fibers after the dissolution of the PLLA matrix indicated that the bonded fibers were PLLA-free.

It is concluded that the bonded fibers produced by this method have the same chemical composition and shape as the original non-bonded ones. Therefore, to screen candidate biomaterials according to scaffolding for cell transplantation, the adhesion, growth, and differentiated function of attached cells can still be tested in vitro with non-bonded fibers before the construction of three-dimensional scaffolds.

EXAMPLE 2: SEEDING OF MATRICES WITH HEPATOCYTES

PGA bonded fiber structures were seeded with hepatocytes for use as transplantation devices for hepatocytes.

Cells were isolated from 180–250 g male Fisher rats using a modification described by Cima, et al., (1991) of the two-step collagenase procedure of Seglen, "Preparation of isolated rat liver cells", *Meth. Cell biol.* 13, 29–83 (1976). Cells were dispersed in chemically defined serum-free culture medium (William's E with 10 ng/ml Epidermal Growth Factor (EGF) (Collaborative Research, Bedford, Mass.), 20 mU/ml insulin (Gibco, Grand Island, N.Y.), 5 nM dexamethasone (Sigma, St. Louis, Mo.), 20 mM pyruvate (Gibco), and 100 U/ml penicillin/streptomycin (Gibco)). This medium was used in all subsequent isolation and culture steps. Cell viability following dispersion was 80–90%, as determined by trypan blue exclusion.

For plating onto polymer meshes, cells were suspended in medium at a concentration of $1 \times 10^7$ cells/ml. The PGA meshes, which are hydrophobic, were prewetted with medium and excess medium was aspirated. A drop of cell suspension (0.1 ml) was placed in the center of a 0.6 cm×0.6 cm square and allowed to wick into the mesh. The meshes were then placed in a humidified 37° C. cell culture incubator with a 5% $CO_2$ environment. Previous studies, Cima, et al., (1991), have shown that cell attachment plateaus after about 1.5 hours, and thus fresh medium was added to completely cover the meshes after a two hour attachment period.

In vitro studies indicated that hepatocytes attached to PGA meshes primarily as individual, isolated cells. There was a high degree of interaction between hepatocytes and fibers 18 hours after plating. By the third day in culture, the cells started to form large clusters and by the end of one week, the major interactions were cell-cell rather than cell-polymer.

Modifications and variations of the method of the present invention, and the products thereof, will be obvious to those skilled in the art from the foregoing detailed description. such modifications and variations are intended to come within the scope of the appended claims.

We claim:

1. A method for making a polymeric matrix suitable for culturing cells comprising providing fibers formed of a first polymer, placing the fibers in a solution of a second polymer, wherein the polymers are synthetic, biocompatible polymers, the second polymer is dissolved in a solvent that is a non-solvent for the first polymer and the melting point of the first polymer is less than the melting point of the second polymer, solidifying the second polymer by removing the solvent to form a matrix of the second polymer around the fibers formed of the first polymer, heating the fiber-matrix to a temperature at which the first polymer melts and maintaining the temperature until the first polymer at the fiber interfaces melts, cooling the first polymer until it solidifies, and dissolving the second polymer and removing the dissolved polymer to leave fibers formed of the first polymer immobilized and bonded at the fiber interfaces.

2. The method of claim 1 wherein the polymers are selected from the group consisting of biodegradable and non-biodegradable polymers.

3. The method of claim 2 wherein the biodegradable polymers are selected from the group consisting of poly(lactic acid) (PLLA), poly(glycolic acid) (PGA), poly(lactide-co-glycolide) (PLGA), polyorthoesters, polyanhydrides, polyphosphazines, and blends and copolymers thereof.

4. The method of claim 2 wherein the non-biodegradable polymers are selected from the group consisting of ethylene vinyl acetate and polymers of acrylic acid and methacrylic acid.

5. The method of claim 1 further comprising seeding the immobilized fibers after removal of the matrix with viable cells for culturing on the substrate formed by the fibers.

\* \* \* \* \*